United States Patent

Tamura et al.

Patent Number: 6,156,466
Date of Patent: *Dec. 5, 2000

[54] PHOTOCONDUCTOR FOR ELECTROPHOTOGRAPHY

[75] Inventors: Shinichi Tamura; Tadashi Mimura; Yoji Yamada; Tadashi Asakawa; Hiroshi Kimura, all of Nagano, Japan

[73] Assignee: Fuji Electric Co., Ltd., Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/111,506

[22] Filed: Jul. 8, 1998

[30] Foreign Application Priority Data

Jul. 10, 1997 [JP] Japan ................... 9-184959

[51] Int. Cl.$^7$ ................... G03G 5/047
[52] U.S. Cl. ................... 430/57.3; 430/57.2
[58] Field of Search ................... 430/57.3, 57.2, 430/59.4, 59.5

[56] References Cited

U.S. PATENT DOCUMENTS

| | | |
|---|---|---|
| 4,847,175 | 7/1989 | Pavlisko et al. ............. 430/59.4 |
| 5,114,815 | 5/1992 | Oda et al. ............. 430/59.5 |
| 5,213,927 | 5/1993 | Kan et al. ............. 430/572 |
| 5,585,483 | 12/1996 | Tamura et al. ............. 540/122 |

OTHER PUBLICATIONS

Borsenberger, Paul M. et al. Organic Photoreceptors for Imaging Systems. New York: Marcel–Dekker, Inc. pp. 289–292, 1993.

Borsenberger, Paul M. and David S. Weiss. Organic Photoreceptors for Imaging Systems. New York: Marcel–Dekker, Inc. pp. 101–107, 338–368, 423, 1993.

*Primary Examiner*—Christopher D. Rodee
*Attorney, Agent, or Firm*—Baker Botts L.L.P.

[57] ABSTRACT

The present invention relates to photoconductors which exhibit excellent electrical properties which are not appreciably affected by environmental changes or by repeated use. Having excellent durability during repeated printing, these photoconductors can be used to obtain large quantities of high-quality output images.

The photoconductor according to the invention includes a conductive substrate and a photoconductive film on the conductive substrate. The photoconductive film includes a plurality of charge generation and transport layers, wherein each layer contains a phthalocyanine compound described in the specification by chemical formula (I) as a charge generation agent and a charge transport agent dispersed or dissolved into a binder. The concentration of the charge generation agent in an upper layer is higher than in a lower layer.

8 Claims, 1 Drawing Sheet

PHOTOCONDUCTOR FOR ELECTROPHOTOGRAPHY

TECHNICAL FIELD OF THE INVENTION

The present invention relates to a photoconductor for use in electrophotography (hereinafter simply referred to as a "photoconductor"). The photoconductors of the present invention can be used in electrophotographic apparatuses such as, printers, copying machines and facsimiles. More specifically, the present invention relates to a positive-charging-type photoconductor which includes an organic photoconductive film.

BACKGROUND OF THE INVENTION

Electrophotography combines the photoconductivity of materials with electrostatic phenomena to form an image, as disclosed in U.S. Pat. No. 2,297,691 to Carlson. Electrophotographic images are generally formed by the following steps: (i) uniformly charging the surface of a photoconductor in the dark by corona-discharge, (ii) forming an electrostatically latent image by exposing the charged surface of the photoconductor to the image, and (iii) depositing colored charge-carrier particles (e.g., toner) onto the electrostatic latent image to convert the latent image into a visible image of the toner. The visible image of the toner is thereafter transferred onto a support such as paper. Electrophotography has been employed widely in copying machines, laser beam printers, and other types of output devices of computers, instruments, and other similar apparatuses.

The photoconductor includes a conductive substrate and a photoconductive film placed onto the conductive substrate. Inorganic photoconductive materials such as amorphous silicon, selenium, zinc oxide and cadmium sulfide have been conventionally used as the main component of the photoconductive film. Unfortunately, however, these traditionally used materials have certain disadvantages. Cadmium sulfide, for example, has been identified to be a potential health hazard, as well as a potential environmental pollutant. In addition, the manufacturing costs associated with the use of silicon and/or selenium (e.g., amorphous silicon, amorphous selenium and/or selenium alloy) are too high due to the required use of the vacuum deposition method or the CVD method in forming such photoconductive films. Furthermore, photoconductive films containing amorphous silicon, amorphous selenium or selenium alloy exhibit poor flexibility.

To obviate the foregoing problems, efforts have been initiated towards investigating the use of organic photoconductors which have a photoconductive film containing an organic photoconductive material dispersed and dissolved into a resin binder. These organic materials are advantageous because (i) there is a wide variety of useful materials, (ii) film formation is easier, (iii) manufacturing costs are decreased, and (iv) the resulting photoconductors are thermally stable. As a result of these advantages, organic photoconductors are predominantly used today.

Photoconductors operate by first generating electric charges in response to received light and then transporting the generated electric charges. Two types of photoconductors which are effective in these functions are mono-layered photoconductors and function-separated photoconductors. Mono-layered photoconductors have a single photoconductive film which exhibits all the above described functions. Function-separated photoconductors have a photoconductive film laminate comprising at least (i) a charge generation layer which generates charge carriers in response to the received light and (ii) a charge transport layer which retains surface potential of the photoconductor in the dark and which neutralizes the surface potential by transporting the charge carriers, which are generated in the charge generation layer. Function-separated photoconductors have been predominantly used recently because appropriate materials can be easily selected for each of the charge generation layer and the charge transport layer. This advantage helps to obtain greater photoconductive sensitivity and, as a result, excellent electrophotographic properties.

Since charge carrier mobility in the charge generation layer is essentially low, it is necessary for the charge generation layer to be substantially 1 $\mu$m or less in thickness. To protect such a thin charge generation layer against wear, practical function-separated photoconductors include a laminate-type photoconductive film in which the charge transport layer is laminated onto the charge generation layer.

At present, the most prevalent type of function-separated photoconductors are negative charging photoconductors because the vast majority of practical charge transport agents available at the present time can only transport holes (e.g., a charge in a substance which is the same amount of and opposite to the charge of an electron). Unfortunately, useful charge transport agent which can transport electrons has not yet been found. Negative-charging-type photoconductors work by forming the image by charging the surface of the photoconductor with a negative electrostatic charge. Typically, corona discharged is used to produce the electrostatic charge.

However, there are several disadvantages with the use of negative corona discharge. First, negative corona discharges are not uniform. As a result, the surface of the photoconductor becomes unevenly charged, and the images obtained therefrom lack smoothness and definition. Secondly, negative corona discharge causes a large amount of ozone (e.g., ten times as much as by the positive corona discharge). Since ozone is thought to cause deterioration of photoconductor surface materials and their resulting electrical properties, a large amount of ozone shortens the life of the photoconductor and decreases the quality of the output images. In addition, a large amount of ozone is thought to be hazardous to the environment.

To obviate the foregoing problems, research has recently been redirected to efforts in finding and/or developing organic photoconductors which can be used in the positive charging mode. Positive-charging-type organic photoconductors may be classified as a mono-layered type (e.g., one which includes a photoconductive film for charge generation and for charge transport) or a function-separated type (e.g., one which includes a photoconductive film including a layer for charge generation and another layer for charge transport).

For example, Japanese Unexamined Laid Open Patent Application No. S48-25658 discloses a mono-layered-type photoconductor which uses poly-N-vinylcarbazole chemically sensitized with an acceptor material such as 2,4,7-trinitrofluorenone (TNF) and tetracyanoquinodimethane (TCNQ). In addition, Japanese Unexamined Laid Open Patent Application No. S47-10785 discloses a mono-layered-type photoconductor which uses an eutectic complex consisting of a pyrylium salt dye and a resin.

However, when an acceptor material such as TNF and TCNQ for sensitizing poly-N-vinylcarbazole is added in sufficient quantities to obtain practical sensitivity, the dark resistance of the photoconductor is decreased by the formation of a charge transfer complex, thereby decreasing the charge level of the photoconductor. Moreover, TNF and TCNQ are thought to be too carcinogenic to be used in general-purpose photoconductors. Similarly, photoconductors containing ionic dye compounds (such as a pyrylium salt or a thiapyrylium salt) are unacceptably sensitive to variations in humidity (e.g., high humidity lowers the level of charge). Therefore, charge transfer complex forming materials and ionic materials are not practical for use as photoconductive materials.

Japanese Examined Patent Application No. S47-42512 discloses a mono-layered-type photoconductor which uses X-type metal-free phthalocyanine, an n-type semiconductor (e.g., containing a semiconducting substance wherein electrons, not holes, are the dominant charge carriers), dispersed in a binder resin. X-type metal-free phthaloxyanine materials are also disclosed in U.S. Pat. No. 3,357,989, which reference is incorporated herein by its entirety. However, this photoconductor poses some problems in its sensitivity and characteristics in repeated use due to its insufficient charge transport capability.

Although pigment-dispersion type photoconductors which use both a hole transport agent and an electron transport agent have been tested to determine whether the charge transport capability can be improved, few useful electron transport agents have been identified for use in photoconductors. Many potential electron transport agents are toxic or carcinogenic. In addition, a large number of electron transport agents used in photoconductive films cause injection of electrons (e.g., having the opposite charge) from the negatively charged substrate. As a result, these electron transport agents lower the resistance of the photoconductive film because charge transfer complexes are formed with the charge generation agent or with the hole transport agent. Inevitably, the charging capability of the photoconductor is impaired.

During use, the photoconductor surface is eroded by repetitive sliding-contact with the toner, carrier paper, and cleaning blade. As the photoconductive film becomes thinner, the problems associated with repeated printing become more prevalent (e.g., a decrease in the potential retention capability and/or a decrease in printing density of the output images). Although a thicker photoconductive film is more durable, the benefits of durability must be balanced with the benefits of photoconductive sensitivity which is adversely affected by an increase in photoconductive film thickness beyond that at which the maximum sensitivity is obtained.

Recently, the function-separated-laminate-type photoconductor has been investigated intensively, because a photoconductor having a photoconductive film, which includes a charge transport layer laminated onto a charge generation layer, can be used in the positive charging mode if a charge transport agent which exhibits excellent electron transport capability is found. However, an electron transport agent having such properties has not yet been found. To obtain a function-separated-laminate-type photoconductor for use in the positive charging mode in light of practical charge transport agents presently available, it is necessary to employ a photoconductive film which includes a charge generation layer laminated onto a charge transport layer exhibiting a hole transport capability. This type of photoconductive film, which has an order of lamination opposite to that in the photoconductor used in the negative charging mode, is called an "inverse-lamination-type photoconductor". As described earlier, the charge generation layer of the function-separated-laminate-type photoconductor should be as thin as 1 µm or less. It is difficult to form such a thin, uniform film. Such a thin film is easily adversely affected by damage, unevenness, stains and deposits such as contaminants on the under layer. Such film defects and uneven film thickness further cause image defects such as uneven printing density, black spots and white streaks. Film defects further decrease productivity and raise manufacturing costs of the photoconductor. As a result, inverse-lamination-type photoconductors, which include such a thin charge generation layer in its surface, exhibit insufficient durability against repeated printing.

Unfortunately, a wear-resistant protection film, which can protect the photoconductor surface from wear, unacceptably increases manufacturing costs by adding an additional manufacturing step. Furthermore, such a protective film adversely affects the electrical properties of the photoconductor because it does not exhibit any charge transport capability. Therefore, a photoconductor having a surface protection film has not yet been used in practice.

Japanese Examined Patent Application No. H05-30262 discloses a photoconductor which obviates the foregoing problems of the mono-layered-dispersion-type photoconductor and the inverse-lamination-function-separated type photoconductor. This photoconductor includes a photoconductive film which further includes a charge transport layer, which contains a hole transport agent, laminated onto a conductive substrate, and a layer, which contains both a charge generation agent and a hole transport agent, laminated onto the charge transport layer. Hereinafter, the layer which exhibits both charge generation and charge transport functions will be referred to as a "charge generation and transport layer". Similarly hereinafter, a photoconductor which includes a charge generation and transport layer laminated on a charge transport layer will be referred to as a "mono-layer-dispersion-type inverse-laminate photoconductor". The mono-layer-dispersion-type inverse-laminate photoconductor improves durability against repeated printing as compared with the inverse-laminate-function-separated-type photoconductor, the surface layer of which only exhibits charge generation function. An increase in durability is seen because the surface layer of the mono-layer-dispersion-type inverse-laminate photoconductor may be set to be thicker than the surface layer of the inverse-laminate-function-separated-type photoconductor. However, when the charge generation and transport layer is too thick, the electrostatic capacity of the photoconductive film lowers and the amount of electrical charges retained in the photoconductive film decreases, even if the potential retention capability is improved. As the amount of electrical charges retained in the photoconductive film decreases, it becomes difficult to attract the toner thereby causing electrical fatigue such as lowered printing density in the output images, lowered sensitivity in repeated use, a rise in residual potential, and variation of charging capability. During use, photoconductor surface wear by the toner and the carrier paper sometimes cause local scratch streaks ten times as deep as the average scratch streak depth. Since electrical charges can not escape from such deep scratch streaks as to reach the charge transport layer, defects like scratches are caused on the output images. Thus, the conventional mono-layer-dispersion-type inverse-laminate photoconductor still fails to be sufficiently durable against repeated printing.

As explained hereinbefore, the conventional positive-charging type photoconductor is impractical as compared to the negative-charging type photoconductor.

In view of the foregoing, it is an object of the invention to provide a positive-charging type photoconductor which exhibits excellent electrical properties and excellent durability during repeated printing.

It is another object of the invention to provide a positive-charging type photoconductor, the characteristics of which are relatively unaffected by the changes of the circumstances and by the repeated use thereof.

It is still another object of the invention to provide a stable positive-charging type photoconductor which facilitates obtaining high-quality output images.

These and other objects of the present invention will become apparent in light of the following disclosure.

SUMMARY OF THE INVENTION

The present invention relates to a photoconductor for electrophotography, which photoconductor comprises a conductive substrate and a photoconductive film placed onto the conductive substrate. The photoconductive film comprises a plurality of layers from lower to upper from the substrate, wherein each of the layers comprises a charge transport agent and a charge generation agent. The concentration of the charge generation agent is higher in the upper layers versus the lower layers. The charge generation agent comprises a phthalocyanine compound described by the following formula (I):

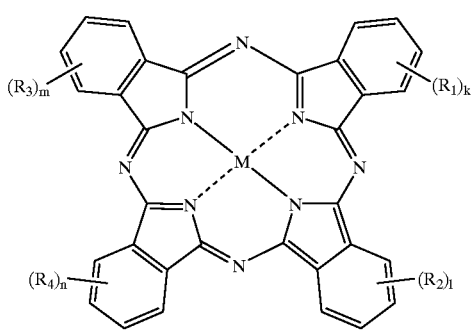

(I)

wherein M is TiO, 2H or Cu; each of $R_1$, $R_2$, $R_3$ and $R_4$ is independently hydrogen or a methyl group; and each of k, l, m and n is independently 0, 1, 2 or 3.

In further embodiments, each layer of said photoconductive films exhibits a charge generation function and a charge transport function.

All percentages and ratios used herein are by weight of the total composition and all measurements made are at 25° C., unless otherwise designated. All weight percentages, unless otherwise indicated, are on an active weight basis. The invention also comprises additional optional ingredients and components described herein.

DETAILED DESCRIPTION OF THE INVENTION

The present invention provides a positive-charging type photoconductor having a layered structure. This type of photoconductor obviates the problems of conventional mono-layer-dispersion-type photoconductors and conventional mono-layer-dispersion-type inverse-laminate photoconductors. The positive-charging-type photoconductors according to the present invention exhibit excellent initial electrical properties such as charging capability, sensitivity and potential retention capability. The photoconductors of the present exhibit excellent durability during repeated printing without appreciable variations in performance due to environmental factors, such as changes in humidity. The invention may be better understood by reference to FIGS. 1 and 2 which illustrate two nonlimiting embodiments.

Figure 1:
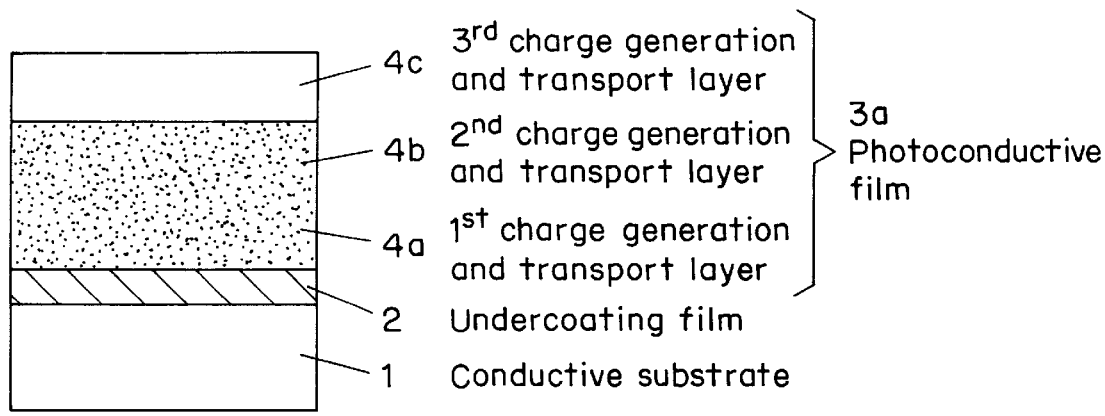
FIG. 1 is a schematic cross section of a photoconductor according to an embodiment of the invention.

FIG. 1 is a schematic cross section of a photoconductor according to one embodiment of the present invention. In FIG. 1, there is shown a conductive substrate 1, an undercoating film 2 on the substrate 1 and a photoconductive film 3a on the undercoating film 2. The photoconductive film 3a includes a first charge generation and transport layer 4a, a second charge generation and transport layer 4b on the first layer 4a, and a third charge generation and transport layer 4c on the second layer 4b. Each charge generation and transport layer contains a charge generation agent, a charge transport agent according to the invention and a binder as its main components. The concentration of the charge generation agent is higher in the upper charge generation/transport layers than in the lower layers.

Figure 2:
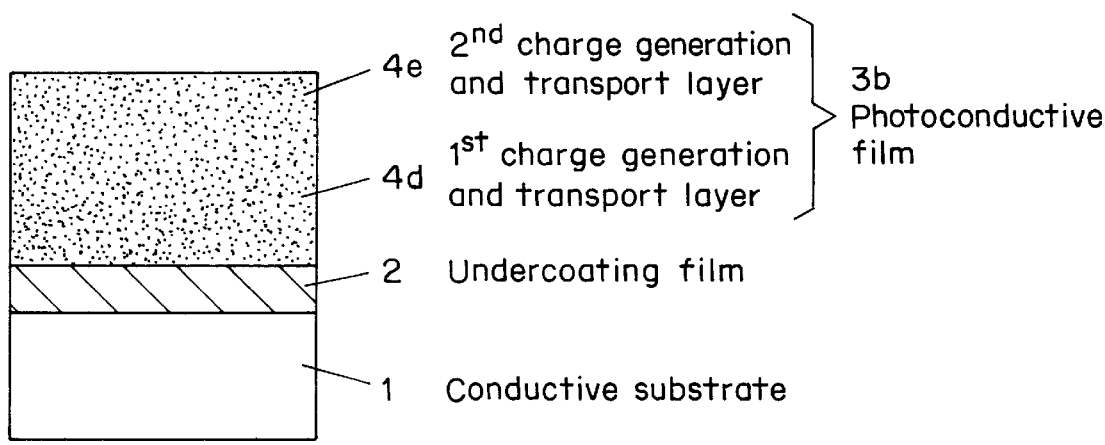
FIG. 2 is a schematic cross section of a photoconductor according to another embodiment of the invention.

FIG. 2 is a schematic cross section of a photoconductor according to another embodiment of the invention. In FIG. 2, there is shown a conductive substrate 1, an undercoating film 2 on the substrate 1 and a photoconductive film 3b on the undercoating film 2. The photoconductive film 3b includes a first charge generation and transport layer 4d and a second charge generation and transport layer 4e on the first layer 4d.

The photoconductors of the present invention comprise a conductive substrate, a photoconductive film, and an optional blocking/undercoating layer.

The Conductive Substrate

The photoconductors of the present invention comprise a conductive substrate. These conductive substrates are thick enough to provide sufficient support for the photoconductive film. Generally, the conductive substrate is about 1 mm. The conductive substrate can be made of any electrically conductive material (e.g., a material exhibiting electroconductive properties). Thus, various electrically conductive materials known to one skilled in the art may be used. The physical form of the electroconductive substrate is also not particularly limited, examples of which include a sheet, a cylindrical tube, a plate or any appropriate desirable shape. Nonlimiting examples of useful electroconductive substrates include metal drums, as well as, metal plates or sheets of aluminum, vanadium, nickel, copper, zinc, palladium, indium, tin, platinum, stainless steel, chrome, and brass. Also useful are drums, plates or sheets of conductive plastics or plastics into which an electrically conductive material is dispersed. Also useful are plastic sheets onto which an electrically conductive material (such as metal powder, carbon black, copper iodide, copper oxide, titanium oxide, indium oxide and alumina) is coated, laminated or deposited. In obtaining these coated or laminated plastic substrates, an appropriate binder, as hereinafter described, may be necessary.

The Photoconductive Film

The photoconductors of the present invention also comprise a photoconductive film which comprises a plurality of layers, preferably from about two to about five layers. Each of these layers provide the dual function of charge generation and charge transport (hereinafter referred to as "charge generation/transport layer"). Since each charge generation/trasport layer provides the dual function of charge generation and charge transport, the thickness limitations of the typical function-separated photoconductor, which have separate charge generation and charge transport layers, do not apply. In one embodiment of the present invention, each charge generation/trasport has a thickness of about 7 microns with the total photoconductive film having a total thickness of about 21 microns for three charge generation/transport layers.

Each charge generation/transport layer contains a charge generation agent and a charge transport agent dispersed or dissolved in a binder. To maintain sufficient sensitivity and yet be durable during repeated printing (e.g., mechanical strength), it is preferable for the charge generation and transport layer to contain the charge generation agent and the charge transport agent at a combined weight ratio of between 7 to 3 and 3 to 7 with respect to the binder.

Furthermore, the concentration of the charge generation agent in each layer increases gradually from the lowermost layer to the uppermost layer from the substrate so that the concentration differences between the upper and lower layers are sufficient enough so as to not resemble a mono-layer dispersion-type photoconductor. The concentration of the charge generation agent in the uppermost layer is preferably about 25 weight % or less with respect to the total weight of the solids in the uppermost layer. The concentration of the charge generation agent in a particular layer is equal to or less than the product of (i) the charge generation agent conentration in the uppermost layer and (ii) the quotient of the total thickness from the substrate to the upper face of a particular layer divided by the total thickness of the photoconductive film (e.g. sum of all of the layers). The concentration range of the charge generation agent is appropriately selected according to the charge generation capability of the charge generation agent and the designed potential retention capability of the photoconductor as a whole.

A. The Charge Generation Agent

The photoconductive films of the present invention comprise a charge generation agent selected from phthalocyanine compounds having the following formula (I):

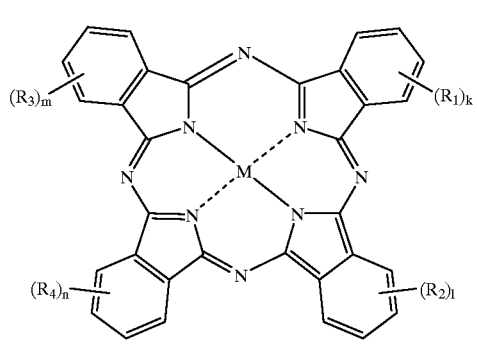

(I)

wherein M is TiO, 2H or Cu; each of $R_1$, $R_2$, $R_3$ and R, is independently hydrogen or a methyl group; and each of k, l, m and n is independently 0, 1, 2 or 3.

Preferably, the phthalocyanine compound is a metal-free phthalocyanine. More preferably, the metal-free phthalocyanine is an X-type metal-free phthalocyanine. Also preferable as the phthalocyanine compound is titanylphthalocyanine. More preferably, the phthalocyanine compound is a titanylphthalocyanine which exhibits a highest peak at 27.2±0.2 degrees of Bragg diffraction angle 2θ on an X-ray diffraction spectrum measured with Cu-K α radiation or a titanylphthalocyanine which exhibits a highest peak at 9.6±0.2 degrees of Bragg diffraction angle 2θ on an X-ray diffraction spectrum measured with Cu-K α radiation.

Phthalocyanine compounds useful herein include metal-free phthalocyanine pigments and titanylphthalocyanine pigments. Preferable metal-free phthalocyanine pigments include X-type metal-free phthalocyanine as disclosed in U.S. Pat. No. 3,357,989 and r-type metal-free phthalocyanine disclosed in the Japanese Unexamined Laid Open Patent Application No. S58-182639. Preferable titanylphthalocyanine pigments include α-types as disclosed in the Japanese Unexamined Laid Open Patent Application No. S61-239248, Y-types as disclosed in Japanese Unexamined Laid Open Patent Application No. H01-17066, I-types as disclosed in Japanese Unexamined Laid Open Patent Application No. S61-109056, A-types as disclosed in Japanese Unexamined Laid Open Patent Application No. S62-67094, C-types as disclosed in Japanese Unexamined Laid Open Patent Applications No. S63-364 and No. S63-366, B-types as disclosed in Japanese Unexamined Laid Open Patent Application No. S61-239248, m-types as disclosed in Japanese Unexamined Laid Open Patent Application No. S63-198067 and a quasi-amorphous-types as disclosed in Japanese Unexamined Laid Open Patent Application No. H01-123868. The other preferable phthalocyanine compound includes ε-type copper phthalocyanine.

B. The Charge Transport Agent

The photoconductive films of the present invention comprise a charge transport agent. Various conventional charge transport agents well known to one of ordinary skill in the art may be used for the photoconductors of the invention. Nonlimiting examples of conventional charge transport agents include hydrazone compounds as disclosed in U.S. Pat. Nos. 4,150,987 and 4,278,747, German Patent Application No. 2 939 483A, British Patent Application No. 2 034 493A and European Patent Application No. 13 172A; pyrazoline compounds and pyrazolone compounds as disclosed in U.S. Pat. No. 3,180,729 and Japanese Unexamined Laid Open Patent Application No. S49-105536; oxadiazole compounds as disclosed in Japanese Unexamined Laid Open Patent Application No. S54-112637; styryl compounds as disclosed in Japanese Unexamined Laid Open Patent Application No. S50-31773; arylamine compounds as disclosed in U.S. Pat. Nos. 3,567,450, 3,180,703, 3,240,597, 3,658,520, 4,232,103, 4,175,961 and 4,012,376, Japanese Examined Patent Application Nos. S49-35702 and S39-27577, West German Patent No. 1 110 518, and Japanese Unexamined Laid Open Patent Application Nos. S55-144250 and S56-119132; oxazole compounds as disclosed in U.S. Pat. No. 3,542,546; and polyarylalkane compounds as disclosed in the U.S. Pat. Nos. 3,615,402, 3,820,989 and 3,542,544 and Japanese Examined Patent Application Nos. S45-555 and S51-10983. Nonlimiting examples of charge transport polymers include poly(vinylpyrene); poly(vinylanthracene); poly(vinylatrazine); poly-9-vinylphenylanthracene; poly(vinylcarbazole) and its derivatives as disclosed in Japanese Examined Patent Application No. S34-10966; polymers of N-acrylamidemethyl-carbazole as disclosed in Japanese Unexamined Laid Open Patent Application No. S50-85337; 6-vinylindol(2,3-6)quinoxaline polymer as disclosed in Japanese Unexamined Laid Open Patent Application No. S50-93432; vinyl polymers as disclosed in Japanese Examined Patent Application Nos. S43-18674 and S43-19192; triphenylmethane polymers as disclosed in Japanese Unexamined Laid Open Patent Application Nos. S56-90883 and S56-161550; styrene copolymers as disclosed in the Japanese Examined Patent Application No. S43-19193; poly(acenaphthene), polyindene; copolymers of acenaphthylene and styrene; and formaldehyde condensed resins as disclosed in the Japanese Examined Patent Application No. S36-13940.

In particular, the hydrazone compounds which are useful in the present invention include P-N-dimethylamino benzaldehyde-N-phenylhydrazone; P-N-diethylaminobenzaldehyde-N-phenyl hydrazone; P-N-diethylaminobenzaldehyde-N,N-diphenylhydrazone, 3-(N-diphenylhydrazone); methyl-9-ethylcarbazole; 3-(N-methyl-N-phenyl hydrazone)-methyl-9-ethylcarbazole; P-N-diethylbenzaldehyde-N,N-ethyl-phenylhydrazone; diethylaminobenzaldehyde-methyl-phenylhydrazone; diethylaminobenzthiazole-carboaldehydediphenylhydrazone; p-diphenyl aminobenzaldehydediphenylhydrazone; p-dibenzylaminobenzaldehyde-diphenylhydrazone; p-(bezyl-methoxyphenyl)aminobenzaldehyde-diphenyl hydrazone; o-methyl-p-diethylaminobenzaldehyde-diphenylhydrazone; o-methoxy-p-diethylaminobenzaldehyde-diphenylhydrazone; o-benzyloxy-p-diethylaminobenaldehyde-diphenylhydrazone; p-diethylaminobenzaldehyde-methyl-phenylhydrazone; o-methyl-p-dibenzylaminobenzaldehyde-methyl-phenylhydrazone; and o-methoxy-p-dibenzylaminobenzaldehyde-phenylhydrazone.

Pyrazoline compounds and pyrazolone compounds which are useful in the present invention include 1-phenyl-3-(p-diethylaminostyryl)-5-(p-diethylaminophenyl)-2Δ-pyrazoline; 1,5-diphenyl-3-methyl-pyrazoline; 1,3,5-triphenylpyrazoline; 1-(β)-naphthyl-3-diphenyl-pyrazoline; 1,5-diphenyl-3-p-oxyphenyl-pyrazoline; 1,3-diphenyl-5-p-methoxyphenyl-pyrazoline; 1-p-ethoxyphenyl-3,5-diphenyl-pyrazoline; 1-m-tolyl-3,5-diphenyl-pyrazoline; 1-p-tolyl-3,5-diphenyl-pyrazoline; 1-phenyl-3-p-methoxy-styryl-5-p-methoxy-phenyl-pyrazoline; 1-phenyl-3-p-dimethylaminostyryl-5-p-dimethylaminophenyl-pyrazoline; 1-p-nitrophenyl-3-p-styryl-5-phenyl-pyrazoline; 1,3-diphenyl-5-(p-dimethyl amino)-phenyl-pyrazoline, 1,5-diphenyl-3-styryl-pyrazoline; 1-phenyl-3-(4-N,N-diethylaminostyryl)-5-(4-N-diethylaminophenyl) pyrazoline; 1-phenyl-3-(4-N,N-dipropylstyryl)-5-(4-N-diethylaminophenyl)pyrazoline; 1-phenyl-3-(4-N,N-dibenzylstyryl)-5-(4-N-diethylaminophenyl)pyrazoline; 1-[pyridyl-(2)]-3-(4-N,N-diethylaminostyryl)-5-(4-N,N-diethylaminophenyl)pyrazoline; 1-[quinolyl-(2)]-3-(4-N,N-diethylaminostyryl)-5-(4-N,N-diethylaminophenyl) pyrazoline; 1-[quinolyl-(4)]-3-(4-N,N-diethylaminostyryl)-5-(4-N, N-diethyl aminophenyl)pyrazoline; 1-[3-methoxy-pyridyl-(2)]-3-(4-N,N-diethylamino styryl)-5-(4-N,N-diethylaminophenyl)pyrazoline; 1-[lepidyl-(2)-3-(4-N,N-diethylaminostyryl)-5-(4-N, N-diethylaminophenyl) pyrazoline; 1-phenyl-3-(4-N,N-diethylaminostyryl)-4-methyl-5-(4-N,N-diethylamino phenyl)pyrazoline; 1-phenyl-3-(α-methyl-4-N,N-diethylaminostyryl)-5-(4-N, N-diethylaminophenyl)pyrazoline; 1-[pyridyl-(3)]-3-(4-N, N-diethyl aminostyryl)-5-(4-N, N-diethylaminophenyl) pyrazoline; and 1-phenyl-3-(α-benzyl-4-N,N-diethylaminostyryl)-5-(4-N,N-diethylaminophenyl) pyrazoline.

The oxadiazole compounds which are useful as charge transport agents include 2,5-bis(4-N,N-dimethylamino phenyl)-1,3,4-oxadiazole; 2,5-bis(4-N,N-dipropylaminophenyl)-1,3,4-oxadiazole; 2,5-bis(4-N,N-diethylaminophenyl)-1,3,4-oxadiazole; 2,5-bis(4-acethylamino-2-chlorophenyl)-1,3,4-oxadiazole; 2,5-bis(4-n-propylamino-2-chlorophenyl)-1,3,4-oxadiazole; 2,5-bis(4-cyclohexylaminophenyl)-1,3,4-oxadiazole; 2,5-bis(4-diethylaminostyryl)-1,3,4-oxadiazole; 2,5-bis(4-N,N-dibenzylaminophenyl)-1,3,4-oxadiazole; 2-methyl-5-(3-carbazolyl)-1,3,4-oxadiazole; 2-ethyl-5-(3-carbazolyl)-1,3,4-oxadiazole; 2-ethyl-5-(9-ethyl-3-carbazole)-1,3,4-oxadiazole; 2-N,N-diethylamino-5-(9-ethyl-3-carbazole)-1,3,4-oxadiazole; and 2-styryl-5-(3-carbazolyl)-1,3,4-oxadiazole.

The arylamine compounds useful herein include triphenylamine; tri-(p-methylphenyl)-amine; tetra-N,N,N',N'-phenyl-benzidine, tetra-N,N,N',N'-phenyl-toluidine; tetra-N, N,N',N'-phenyl-dichlorobenzidine; tetra-N,N,N',N'-tolyl-benzidine; and tetra-N,N,N',N'-tolyl-toluidine.

The oxazole compounds useful herein include 2-(4-N,N-diethylaminophenyl)-4-(4-N,N-dimethylaminophenyl)-5-(2-chlorophenyl)oxazole; 2-(4-N,N-diethyl aminophenyl)-5-phenyloxazole; 4-(4-N,N-dimethylaminophenyl)-5-(2-chlorophenyl)oxazole; 2-(4-N,N-dimethylaminophenyl)-4,5-diphenyloxazole; and 2-(4-N,N-diethylaminophenyl)-4-(4-N,N-diethylaminophenyl)oxazole.

The arylalkane compounds useful herein include 1,1-bis(4-N,N- dimethylaminophenyl)propane; 1,1-bis(4-N,N-diethylaminophenyl)propane, 1,1-bis(4-N,N-diethylamino-2-methylphenyl)propane; 1,1-bis(4-N,N-diethylamino-2-methoxyphenyl)propane; 1,1-bis(4-N,N-dibenzylamino-2-methoxyphenyl)-2-methylpropane; 1,1-bis(4-N,N-diethylamino-2-methyl phenyl)-2-phenylpropane; 1,1-bis(4-N,N-diethylamino-2-methylphenyl) heptane; 1,1-bis(4-N, N-dibenzylamino-2-methylphenyl)-1-cyclohexyl methane; 1,1-bis(4-N,N-dimethylaminophenyl)pentane; and 1,1-bis (4-N,N- dibenzylaminophenyl)normalheptane.

The triarylalkane compounds useful herein include 1,1-bis(4-N,N-dimethylamino phenyl)-1-phenylmethane; 1,1-bis(4-N,N-diethylaminophenyl)-1-phenyl methane; 1,1-bis(4-N,N-diethylamino-2-methylphenyl)-1-phenylmethane; 1,1-bis(4-N,N-diethylamino-2-ethylphenyl)-2-phenylmethane; 1,1-bis(4-N,N-diethylamino-2-methylphenyl)-3-phenylpropane; and 1,1-bis(4-N,N-diethylamino-2,5-dimethoxyphenyl)-3-phenylpropane.

Other compounds which are also useful herein as charge transport agents include butadiene compounds such as 1,1-bis(p-dimethylaminophenyl)-4,4-diphenyl-1,3-butadiene and 1,1-bis(p-diethylaminophenyl)-4,4-diphenyl-1,3-butadiene; anthracene compounds such as 9-styrylanthracene, 9-(4-N,N-dimethylaminostyryl)anthracene, 9-(4-N,N-diethylaminostyryl)anthracene, 9-(4-N,N-dibenzylaminostyryl)anthracene, 4-bromo-9-(4-N,N-diethylamino styryl)anthracene; α-(9-antryl)-β-(3-carbazolyl)ethylene; and α-(9-antryl)-β-(9-ethyl-3-carbazolyl)ethylene; stilbene compounds such as 4,4'-bis(diethylamino)stilbene, 4-diphenylamino-4'methoxystilbene and 4-diethylamino-α-(p-diethylaminophenyl)stilbene; and 3-(p-methoxystyryl)-9-p-methoxyphenylcarbazole.

The diphenoquinone compounds disclosed in Japanese Unexamined Laid Open Patent Application Nos. H05-279285, H05-148214 and H05-306262 are also useful as electron transport agents.

The charge transport agents adaptable to the photoconductor of the invention are not limited to those described above. The charge transport agents described above may be used alone or in an appropriate combination.

C. The Binder

Because the foregoing charge transport agents and charge generation agents may be difficult to form into a film onto the conductive substrate, a charge generation and transport layer is formed by coating a liquid prepared by dispersing or dissolving a charge transport agent and a charge generation agent into an appropriate binder. Preferable binders include hydrophobic and highly insulative polymers and copolymers which facilitate forming a film. In detail, the preferable binders include phenolic resin, polyester resin, vinyl acetate resin, polycarbonate resin, polypeptide resin, cellulose resin, poly(vinyl pyrrolidone), polyethylene oxide, poly(vinyl chloride) resin, poly(vinylidene chloride) resin, polystyrene resin, poly(vinyl acetate), styrene-butadiene copolymer, vinylidene chloride-acrylonitrile copolymer, vinyl chloride-vinyl acetate copolymer, vinyl chloride-vinyl acetate-maleic anhydride copolymer, silicone-alkyd resin, phenol-formaldehyde resin, ethylene-alkyd resin, poly(vinyl alcohol), acrylic copolymer resin, methacrylic copolymer resin, silicone resin, methacrylonitrile copolymer resin, and poly(vinyl butyral). Polycarbonate, polybutyral and poly (vinyl formal) resins are more preferred.

Since the binder is contained at the heaviest weight ratio in the charge generation and transport layer, the properties of the binder greatly affect the properties of the photoconductor. For maintaining electrical properties and durability during repeated printing, polycarbonate, polybutyral and poly(vinyl formal) resins are preferable. Polycarbonate resin is especially preferable in the photoconductors of the present invention, since polycarbonate resin exhibits excellent electrical properties, such as sensitivity, as well as excellent durability against repeated printing.

The binders described above may be used alone or in an appropriate combination.

D. Doping Ingredients

The charge generation and transport layer may also be doped with various ingredients, such as antioxidants and light stabilizers for preventing deterioration caused by ozone produced by corona discharge, nitrogen oxides ($NO_x$) or light, plasticizers and leveling agents.

Useful antioxidants include chromanol derivatives such as tocopherol, ether compounds of the chromanol derivatives, esterified compounds of the chromanol derivatives, polyarylalkane compounds, hydroquinone derivatives, monoether compounds of the hydroquinone derivatives, diether compounds of the hydroquinone derivatives, benzophenone derivatives, benzotriazole derivatives, thioether compounds, phosphonic esters, phosphites, phenylenediamine derivatives, phenol compounds, hindered phenol compounds, linear amine compounds, cyclic amine compounds, and hindered amine compounds. In detail, hindered phenol compounds such as IRGANOX1010 (supplied from Ciba Geigy Japan, Ltd.), IRGANOX565 (supplied from Ciba Geigy Japan, Ltd.) and SUMILYZER-MDP (supplied from Sumitomo Chemical Co., Ltd.) and hindered amine compounds such as SANOL LS-622LD (supplied from Sankyo Co., Ltd.) and SANOL LS-2626 (supplied from Sankyo Co., Ltd.) are used.

Preferably, an organic acceptor compound is contained in the charge generation and transport layer to lower the residual potential and to improve the sensitivity. Useful organic acceptor compounds include compounds exhibiting a large electron affinity, such as succinic anhydride, maleic anhydride, dibromosuccinic anhydride, phthalic anhydride, 3-nitrophthalic anhydride, 4-nitrophthalic anhydride, pyromellitic anhydride, pyromellitic acid, trimellitic acid, trimellitic anhydride, phthalimide, 4-nitrophthalimide, tetracyanoethylene, tetracyanoquinodimethane, chloranil, bromanil, o-nitrobenzoic acid, and p-nitrobenzoic acid.

The Blocking Layer or Undercoating Layer

The photoconductors of the present invention can optionally comprise a "blocking layer" or an "undercoating layer", which is interposed between the conductive substrate and the charger generation and transport layer to prevent charge injection from the conductive substrate to the charge generation and transport layer. This blocking/undercoating layer also improves the adhesiveness between the conductive substrate and the charge generation and transport layer.

Useful materials for the undercoating layer include metal oxides such as anodized alumina, and resins which can be formed easily as a film. Nonlimiting examples of such resins include polyamide such as nylon 6, nylon 66, nylon 11, nylon 610, copolymerized nylon and alkoxymethylated nylon (these nylons are well known to those skilled in the art); casein; poly(vinyl alcohol); poly(vinyl butyral); ethylene-acrylic acid copolymer; acrylic resin; methacrylic resin; vinyl chloride resin; phenol resin; epoxy resin; polyester resin; alkyd resin;, polycarbonate resin; urethane resin; polyimide resin; vinylidene chloride resin; vinyl chloride-vinyl acetate copolymer; gelatin; nitrocellulose; and water-soluble ethylene-acrylic acid copolymer. Conductive, semi-conductive or dielectric particles such as zinc oxide, titanium oxide, aluminum oxide; silicon nitride, silicon carbide and carbon black may also be dispersed into the foregoing resins for the undercoating layer. The blocking or undercoating layer is preferably form 0.1 to 10 µm in thickness, and, more preferably, form 0.5 to 3 µm in thickness.

Method of Manufacture

The charge generation/transport layer of the invention is formed by coating on a conductive substrate a coating liquid, prepared by dispersing or dissolving a charge transport agent, a charge generation agent, a binder and, if necessary, additional ingredients into an appropriate solvent, with conventional coating instruments, such as a dip coater, a spray coater, a wire-bar coater, an applicator, a doctor blade, a roller coater, a curtain coater and a bead coater. The resulting coated conductive substrate is then dried by conventional means.

Solvents useful herein in the coating liquid include toluene, xylene, monochlorobenzene, 1,2-dichloroethane, dichloromethane, 1,1,1-trichloroethane, 1,1,2-trichloroethylene, tertrahydrofuran, methyl ethyl ketone, cyclohexanone, ethyl acetate, and butyl acetate.

The instruments useful for dispersing or for dissolving the ingredients of the coating liquid include an attriter, a ball mill, a sand mill, a high-speed mixer, a Banbury mixer, a spec mixer, a roll mill, a three-roll mill, an nanomizer, a stumble mill, an epicyclical mill, and a vibration mill. Dispersing media such as glass beads, steel beads, zirconia beads, alumina balls, zirconia balls and flint stones may be additionally employed, if necessary.

A more extensive description of the methods of manufacturing the photoconductors of the present innvetion is provided in the following Examples.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1 (E1)

Three kinds of coating liquids "a", "b" and "c" (each having different concentrations of the charge generation agent) were prepared by mixing X-type metal-free phthalocyanine as a charge generation agent, tetra-N,N,N',N'-phenyl-toluidine, as shown in structural formula (II), as a charge transport agent and polycarbonate resin (IUPILON PCZ-200 supplied from MITSUBISHI GAS CHEMICAL COMPANY, INC.) as a binder at the composition ratios listed in Table 1, and by masticating the mixtures with 1000 weight parts of tetrahydrofuran in a ball mill.

(II)

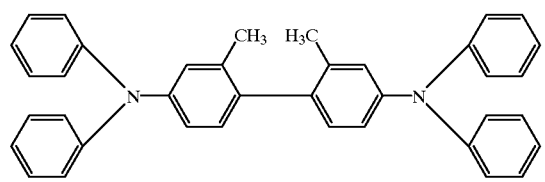

TABLE 1

Composition of the Coating Liquid

|  | Coating liquid "a" | Coating liquid "b" | Coating liquid "c" |
|---|---|---|---|
| Charge generation agent | 1 weight part | 2 weight parts | 5 weight parts |
| Charge transport agent | 40 weight parts | 40 weight parts | 40 weight parts |
| Binder | 59 weight parts | 58 weight parts | 55 weight parts |

These coating liquids were used for fabricating photoconductors having the structure illustrated in FIG. 1.

A coating liquid for an undercoating film was prepared by dissolving 1 part by weight of copolymerized polyamide (Amilan CM8000 supplied from TORAY INDUSTRIES, INC.) in 100 parts by weight of ethanol. An undercoating film 2 of 0.2 μm in thickness was formed by first coating the coating liquid on a cylindrical tubular conductive substrate 1 of aluminum and then drying the coating liquid onto the conductive substrate.

A first charge generation and transport layer 4a of 7 μm in thickness was formed on top of the undercoating film 2 by dip-coating and drying coating liquid "a" onto the undercoating film 2. A second charge generation and transport layer 4b of 7 μm in thickness was formed on top of the first charge generation and transport layer 4a by dip-coating and drying coating liquid "b" on top of the layer 4a. Then, a third charge generation and transport layer 4c of 7 μm in thickness was formed on top of the second charge generation and transport layer 4b by dip-coating and drying coating liquid "c" on top of the layer 4b. Thus, a photoconductor E1 having a triple-layered photoconductive film, as shown in FIG. 1, of 21 μm in thickness was fabricated.

The hereinbefore described photoconductor E1 was evaluated in the following way as a photo-semiconductor in terms of the initial electrical properties. The photoconductor was mounted on a commercially-available semiconductor-laser-beam printer, the charging device thereof having been changed to a scorotron charging device working at a corona discharge voltage of +6.5 kV and a grid voltage of +800 V such that the printer operates in a positive charging mode. After the photoconductor surface was charged, the surface potential of the charged photoconductor not exposed to any laser beam was measured as a dark potential at the position of the development device. After the dark potential measurement, the surface was irradiated via a 780 nm laser beam with irradiation energy of 0.4 μJ/cm², and the surface potential was measured as a bright potential at the position of the development device. The dark potential data was used for evaluating the charging capability of the photoconductor, and the bright potential data was used for evaluating the sensitivity of the photoconductor. Then, the photoconductor was subjected to a durability test by printing 20,000 sheets of A4 size paper. Electrical properties were measured and image qualities were evaluated before and after the test. The durability of the photoconductor was evaluated by the variations of the electrical properties and the image qualities before and after the test. Table 2 lists the results.

As Table 2 indicates, the photoconductor E1 exhibited excellent initial charging capability and excellent sensitivity. The properties of the photoconductor E1 changed little after undergoing the printing durability test. Furthermore, the image qualities of the photoconductor E1 exhibited little deterioration before and after the test. Thus, the photoconductor E1 according to the Example 1 is a practical one which exhibits excellent electrical properties and excellent durability.

Example 2 (E2)

An undercoating film 2 was formed in a similar manner as the undercoating film 2 of Example 1 on a cylindrical tubular conductive substrate 1 of aluminum. A first charge generation and transport layer 4d of 14 μm in thickness was formed on the undercoating film 2 by dip-coating and drying the coating liquid "a" onto the undercoating film 2. Then, a second charge generation and transport layer 4e of 7 μm in thickness was formed on the first charge generation and transport layer 4d by dip-coating and drying the coating liquid "c" on top of the layer 4d. Thus, a photoconductor E2 having a double-layered photoconductive film, as shown in FIG. 2, of 21 μm in thickness was fabricated.

The photoconductor E2 was evaluated in the same manner as the photoconductor according to the Example 1. The results are described in Table 2.

As Table 2 indicates, the photoconductor E2 exhibited excellent initial charging capability and excellent sensitivity. The properties of the photoconductor E2 changed little by the printing durability test. The image qualities of the photoconductor E2 exhibited little deterioration before and after the test. Thus, the photoconductor E2 is a practical one which exhibits excellent electrical properties and excellent durability.

Comparative Example 1 (C1)

An undercoating film was formed in a similar manner as the undercoating film 2 of the photoconductor E1 on a cylindrical tubular conductive substrate of aluminum. A coating liquid for a charge transport layer was prepared by dissolving 40 parts by weight of the charge transport agent used in the Example 1 and 40 parts by weight of the binder used in the Example 1 in 1,000 parts by weight of tetrahydrofuran. A charge transport layer of 20 μm in thickness was formed on the undercoating layer by dip-coating and by drying the coating liquid. A coating liquid for a charge generation layer was prepared by dissolving 60 parts by weight of the binder used in the Example 1 in 2,000 parts by weight of tetrahydrofuran and by dispersing 40 parts by weight of X-type metal-free phthalocyanine into the above described solution by ball-milling. A charge generation layer of 1 μm in thickness was formed on the charge transport layer by spray-coating and then drying the coating liquid. Thus, an inverse-laminate-type photoconductor C1, which includes a photoconductive film having a charge generation layer on a charge transport layer, was fabricated.

The photoconductor C1 as evaluated in the same manner as photoconductor E1 in Example 1. The results are described in Table 2.

As Table 2 indicates, photoconductor C1 exhibited similar initial properties as those of the photoconductor according to the Example 1. However, during the printing durability test, many white streaks were caused on the solid black background after 500 sheets of printing. Therefore, comparative photoconductor C1 can not be used in practice.

Comparative Example 2 (C2)

A photoconductor C2 according to Comparative Example 2 was fabricated in a similar manner as photoconductor C1 except that the charge transport layer was 14 μm in thickness and the charge generation layer was 7 μm in thickness in the photoconductor C2. Photoconductor C2 was evaluated in the same manner as photoconductor E1. The results are listed in Table 2.

As Table 2 indicates, the initial bright potential was almost the same as the initial dark potential in the photoconductor C2. Therefore, the photoconductor C2 does not exhibit any photoconductive sensitivity and, therefore, lacks any printing capability.

Comparative Example 3 (C3)

A coating liquid for a charge transport layer which does not contain any charge generation agent was prepared by replacing the charge generation agent in the foregoing coating liquid "a" with the same amount of the charge transport agent. A photoconductor C3 was fabricated in a similar manner as photoconductor E1 according to the Example 1 except that a charge transport layer of 14 μm in thickness was formed using the coating liquid prepared as described above and a charge generation and transport layer of 7 μm in thickness was formed using the foregoing coating liquid "c" on top of the charge transport layer such that a photoconductive film of 21 μm in thickness was formed. Photoconductor C3 was evaluated in the same manner as photoconductor E1. The results are listed in Table 2.

As Table 2 indicates, although the initial properties and the initial output image quality of the photoconductor C3 were excellent, several important factors changed during the printing durability test: (i) the bright potential was increased greatly, (ii) the photoconductive sensitivity decreased, (iii) the solid black background density decreased, and (iv) many white streaks, not covered with the toner were encountered. Therefore, photoconductor C3 is not well suited for practical use.

Comparative Example 4 (C4)

A photoconductor C4 was fabricated in the same manner as the photoconductor E1 except that the photoconductive film of photoconductor C4 was a mono-layered one of 21 μm in thickness consisting of a charge generation/transport layer formed using the foregoing coating liquid "c". Photoconductor C4 was evaluated in the same manner as the photoconductor E1. The results are listed in Table 2.

As Table 2 indicates, photoconductor C4 exhibited excellent initial properties. However, dark potential was greatly decreased (e.g., as large as 350 V), which further caused a great decrease in charging capability, and the bright potential increased to a value twice as high as the initial value after the printing durability test. The density of the output images decreased and the white background not irradiated by the exposure light was covered with a thin toner layer. Therefore, photoconductor C4 poses too many problems for practical use.

Example 3 (E3)

A photoconductor E3 was fabricated in the same manner as photoconductor E1 except that Y-type titanylphthalocyanine exhibiting a highest diffraction peak at 27.2 degrees of Bragg angle 2θ on an X-ray diffraction spectrum measured with Cu-K α radiation was used for the charge generation agent in photoconductor E3. Photoconductor E3 was evaluated in the same manner as photoconductor E1. The results are listed in Table 2.

As Table 2 indicates, photoconductor E3 exhibited excellent electrical properties and excellent durability after repeated printing, as well as excellent initial properties. These resuls are similar to the test results for photoconductors E1 and E2.

Comparative Example 5 (C5)

A photoconductor C5 was fabricated in the same manner as photoconductor C3 except that Y-type titanylphthalocyanine of Example 3 was used for the charge generation agent in photoconductor C5. Photoconductor C5 was evaluated in the same manner as photoconductor E1. The results are listed in Table 2.

As Table 2 indicates, although the initial properties and the initial output image quality of photoconductor C5 were excellent, the data changed during the printing durability test: (i) the bright potential greatly increased, (ii) the sensitivity decreased, (iii) the density of solid black background lowered, and (iv) many white streaks, not covered with the toner, were encountered. Therefore, photoconductor C3 is not well suited for practical use.

Comparative Example 6 (C6)

A photoconductor C6 was fabricated in the same manner as photoconductor C4 except that Y-type titanylphthalocyanine of the Example 3 was used for the charge generation agent in photoconductor C6. Photoconductor C6 was evaluated in the same manner as photoconductor E1. The results are listed in Table 2.

As Table 2 indicates, photoconductor C5 exhibited as excellent initial properties and excellent qualities in the initial output images as photoconductor C4. However, dark potential decreased dramatically (e.g., as large as 350 V), which caused a large decrease in charging capability. In addition, bright potential rose to a value threefold as high as the initial value after undergoing the printing durability test. The density of the output images was lowered and the white background not irradiated by the exposure light was covered with a thin toner layer. Therefore, the photoconductor C6 poses to many problems for practical use.

Example 4 (E4)

A photoconductor E4 was fabricated in the same manner as photoconductor E2 according to the Example 2 except that α-type titanylphthalocyanine was used for the charge generation agent and p-diphenylaminobenzaldehyde-diphenylhydrazone described by structural formula (III) was used for the charge transport agent in photoconductor E4.

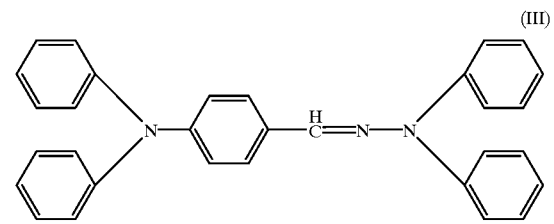

(III)

Photoconductor E4 was evaluated in the same manner as photoconductor E1. The results are listed in Table 2.

As Table 2 indicates, photoconductor E4 exhibited excellent properties and excellent durability during repeated printing. These results were similar to the test results for the photoconductors of the previous Examples.

Example 5 (E5)

A photoconductor E5 was fabricated in the same manner as photoconductor E4 except that titanylphthalocyanine as described in Japanese Unexamined Laid Open Patent Application No. H08-145384 and exhibiting a highest diffraction peak at 9.6 degrees of Bragg angle 2θ on an X-ray diffraction spectrum measured with Cu-K α radiation was used for the charge generation agent in the photoconductor E5. Photoconductor E5 was evaluated in the same manner as photoconductor E1. The results are listed in Table 2.

As Table 2 indicates, photoconductor E5 exhibited excellent electrical properties and excellent durability during repeated printing. These results were similar to the test results for the photoconductors of the previous Examples.

TABLE 2

Summary of Testing Results

| Photo-conductors | Initial Properties | | | Properties after the Printing Test | | |
|---|---|---|---|---|---|---|
| | Dark Potential (V) | Bright Potential (V) | Image Quality | Dark Potential (V) | Bright Potential (V) | Image Quality |
| E1 | 895 | 85 | ○ | 846 | 83 | ○ |
| E2 | 897 | 94 | ○ | 852 | 92 | ○ |
| C1 | 865 | 67 | ○ | — | — | x |
| C2 | 865 | 742 | x | — | — | x |
| C3 | 896 | 92 | ○ | 779 | 352 | Δ–x (White streaks) |
| C4 | 899 | 120 | ○ | 543 | 233 | x (Fogs) |
| E3 | 887 | 65 | ○ | 847 | 47 | ○ |
| C5 | 873 | 88 | ○ | 731 | 347 | x (White streaks) |
| C6 | 888 | 98 | ○ | 539 | 332 | x (Fogs) |
| E4 | 894 | 113 | ○ | 873 | 134 | ○ |
| E5 | 886 | 82 | ○ | 881 | 110 | ○ |

As explained above, the photoconductor according to the present invention includes a conductive substrate and a photoconductive film on the conductive substrate, the photoconductive film including a plurality of charge generation and transport layers laminated one on top of another, each layer containing a phthalocyanine compound described by general formula (I) as a charge generation agent and a charge transport agent dispersed or dissolved into a binder. The concentration of the charge generation agent in an upper layer is higher than in a lower layer. The structure described above facilitates obtaining a positive-charging type photoconductor which exhibits excellent electrical properties, little change of the properties by environmental changes or by repeated use and excellent durability against repeated printing, and facilitates obtaining high-quality output images.

What is claimed is:

1. A photoconductor for electrophotography comprising:

(A) a conductive substrate; and (B) a photoconductive film on said conductive substrate, said photoconductive film consisting of a plurality of charge generation/transport layers from lower to upper, wherein each layer of said film (1) exhibits both a charge generation function and a charge transport function and (2) comprises both (i) a charge transport agent and (ii) a charge generation agent comprising a phthalocyanine compound described by the following formula:

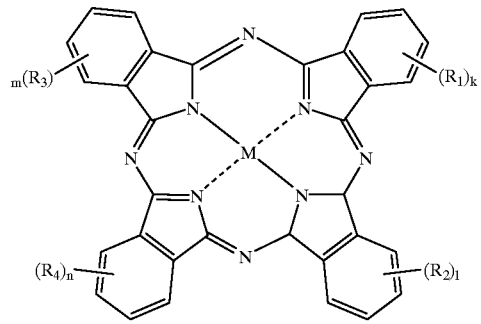

wherein

M is TiO, 2H or Cu;

each of $R_1$, $R_2$, $R_3$, and $R_4$ is independently hydrogen or a methyl group; and each of k, l, m and n is independently 0, 1, 2 or 3; and wherein the concentration of said charge generation agent is higher in the upper layers versus the lower layers.

2. The photoconductor according to claim 1, wherein the concentration of said charge generation agent in an uppermost layer is less than or equal to about 25 weight % with respect to the total weight of the solids in said uppermost layer.

3. The photoconductor according to claim 1, wherein the concentration of said charge generation agent in a particular layer is equal to or less than the product of (i) the charge generation agent concentration in the uppermost layer and (ii) the quotient of the total thickness from the substrate to the upper face of the particular layer divided by the sum of the thicknesses of all of the layers in said photoconductive film.

4. The photoconductor according to claim 1, wherein said phthalocyanine compound is metal-free phthalocyanine.

5. The photoconductor according to claim 4, wherein said metal-free phthalocyanine is a X-type metal-free phthalocyanine.

6. The photoconductor according to claim 1, wherein said phthalocyanine compound is titanylphthalocyanine.

7. The photoconductor according to claim 6, wherein said titanylphthalocyanine exhibits a highest peak at 27.2±0.2 degrees of Bragg diffraction angle 2θ on an X-ray diffraction spectrum measured with Cu-K α radiation.

8. The photoconductor according to claim 7, wherein said titanylphthalocyanine exhibits a highest peak at 9.6±0.2 degrees of Bragg diffraction angle 2θ on an X-ray diffraction spectrum measured with Cu-K α radiation.

* * * * *